(12) United States Patent
Rytter et al.

(10) Patent No.: US 8,921,252 B2
(45) Date of Patent: Dec. 30, 2014

(54) FISCHER-TROPSCH CATALYST REGENERATION

(75) Inventors: Erling Rytter, Trondheim (NO); Sigrid Eri, Ranheim (NO); Torild Hulsund Skagseth, Ranheim (NO); Oyvind Borg, Trondheim (NO)

(73) Assignee: GTLFI AG, Zurich (DE)

( * ) Notice: Subject to any disclaimer, the term of this patent is extended or adjusted under 35 U.S.C. 154(b) by 0 days.

(21) Appl. No.: 13/817,501

(22) PCT Filed: Aug. 17, 2011

(86) PCT No.: PCT/GB2011/001230
§ 371 (c)(1),
(2), (4) Date: Apr. 24, 2013

(87) PCT Pub. No.: WO2012/022942
PCT Pub. Date: Feb. 23, 2012

(65) Prior Publication Data
US 2013/0210939 A1    Aug. 15, 2013

(30) Foreign Application Priority Data
Aug. 19, 2010   (GB) .................................. 1013924.4

(51) Int. Cl.
| | | |
|---|---|---|
| *B01J 38/12* | (2006.01) | |
| *C10G 3/00* | (2006.01) | |
| *B01J 23/94* | (2006.01) | |
| *B01J 33/00* | (2006.01) | |
| *B01J 35/02* | (2006.01) | |
| *B01J 35/10* | (2006.01) | |
| *B01J 38/10* | (2006.01) | |
| *C07C 1/04* | (2006.01) | |
| *C10G 2/00* | (2006.01) | |
| *B01J 23/00* | (2006.01) | |
| *B01J 23/75* | (2006.01) | |

(52) U.S. Cl.
CPC . *C10G 3/62* (2013.01); *B01J 23/94* (2013.01); *B01J 33/00* (2013.01); *B01J 35/023* (2013.01); *B01J 35/1014* (2013.01); *B01J 35/1038* (2013.01); *B01J 38/10* (2013.01); *B01J 38/12* (2013.01); *C07C 1/045* (2013.01); *C10G 2/332* (2013.01); *B01J 23/005* (2013.01); *B01J 23/75* (2013.01); *C07C 2521/04* (2013.01); *C07C 2523/36* (2013.01); *C07C 2523/42* (2013.01); *C07C 2523/75* (2013.01); *C07C 2523/889* (2013.01); *C07C 2523/89* (2013.01); *Y10S 502/514* (2013.01); *Y10S 502/518* (2013.01)
USPC .............................. 502/38; 502/514; 502/518

(58) Field of Classification Search
USPC ....................................... 502/38, 33, 514, 518
See application file for complete search history.

(56) References Cited

U.S. PATENT DOCUMENTS

| | | |
|---|---|---|
| 3,754,993 A | 8/1973 | Oguchi et al. |
| 3,826,739 A | 7/1974 | Kubo et al. |
| 3,915,840 A | 10/1975 | Gladrow et al. |
| 4,670,414 A | 6/1987 | Kobylinski et al. |
| 4,729,981 A | 3/1988 | Kobylinski et al. |
| 4,888,316 A | 12/1989 | Gardner et al. |
| 5,157,054 A | 10/1992 | Herbolzheimer et al. |
| 5,260,239 A | 11/1993 | Hsia |
| 5,268,344 A | 12/1993 | Pedrick et al. |
| 5,283,216 A | 2/1994 | Mitchell |
| 6,022,755 A | 2/2000 | Kinnari et al. |
| 7,045,554 B2 | 5/2006 | Raje et al. |
| 2002/0183403 A1 | 12/2002 | Huang et al. |
| 2003/0166451 A1 | 9/2003 | Koveal et al. |
| 2004/0127585 A1 | 7/2004 | Raje |

FOREIGN PATENT DOCUMENTS

| | | |
|---|---|---|
| CN | 101703937 A | 9/2009 |
| EP | 0 319 625 A1 | 12/1987 |
| WO | WO9414537 | 7/1994 |
| WO | WO 2005/072866 A1 | 8/2005 |
| WO | WO 2008/139407 A2 | 11/2008 |
| WO | WO 2010/070475 A1 | 6/2010 |

OTHER PUBLICATIONS

Saib A M et al: "Fundamental understanding of deactivation and regeneration of cobalt Fischer-Tropsch synthesis catalysts" Catalysis Today, Elsevier, NL, vol. 154, No. 3-4, Mar. 15, 2010, pp. 271-282, XP027197224, ISSN: 0920-5861.

*Primary Examiner* — Edward Johnson
(74) *Attorney, Agent, or Firm* — Patterson Thuente Pedersen, P.A.

(57) ABSTRACT

A process for the regeneration of deactivated catalyst from a Fischer-Tropsch synthesis reactor, the catalyst being a supported cobalt catalyst. The process comprises the following steps: a withdrawal step, in which a portion of deactivated catalyst together with liquid hydrocarbon is withdrawn from the reactor; a concentration step, in which the concentration of the catalyst in the liquid hydrocarbon is increased; a calcination step, in which the deactivated catalyst composition is subjected to an oxidizing gas to oxidize carbonaceous material contained in the deactivated catalyst in to gaseous oxides of the components of the carbonaceous material; and a reactivation step, in which the deactivated catalyst composition is reactivated to produced a regenerated catalyst.

47 Claims, No Drawings

US 8,921,252 B2

FISCHER-TROPSCH CATALYST REGENERATION

The present application is a National Phase entry of PCT Application No. PCT/GB2011/001230 filed Aug. 17, 2011, which claims priority from GB Application No. 1013924.4, filed Aug. 19, 2010, the disclosures of which are hereby incorporated by reference in their entireties.

FIELD OF THE INVENTION

The present invention relates to supported catalysts and their use in Fischer-Tropsch (FT) synthesis reactions, and more specifically to processes for the regeneration of spent catalysts.

BACKGROUND OF THE INVENTION

Conversion of natural gas to liquid hydrocarbons ("Gas To Liquids" or "GTL" process) is based on a 3 step procedure consisting of: 1) synthesis gas production; 2) synthesis gas conversion by FT synthesis; and 3) upgrading of FT products (wax and naphtha/distillates) to final products.

The Fischer-Tropsch reaction for conversion of synthesis gas, a mixture of CO and hydrogen, possibly also containing essentially inert components like $CO_2$, nitrogen and methane, is commercially operated over catalysts containing the active metals Fe or Co. Iron catalysts are best suited for synthesis gas with low $H_2$/CO ratios (<1.2), e.g. from coal or other heavy hydrocarbon feedstock, where this ratio is considerably lower than the consumption ratio of the FT reaction (2.0-2.1). A variety of products can be made by the FT-reaction, but from supported cobalt, the primary product is long-chain hydrocarbons that can be further upgraded to products like diesel fuel and petrochemical naphtha. By-products can include olefins and oxygenates.

To achieve sufficient catalytic activity, it is customary to disperse the Co on a catalyst carrier, often referred to as the support material. In this way, a larger portion of Co is exposed as surface atoms where the reaction can take place. Supported cobalt catalysts are the preferred catalysts for the FT synthesis. The most important properties of a cobalt FT catalyst are the activity, the selectivity usually to C5 and heavier products, i.e. C5+, and the resistance towards deactivation. The physical strength and chemical robustness of the catalyst and support are also crucial. Normally, the catalyst is deployed in a slurry type, fluidized bed or fixed-bed reactor when used, but other reactor types like a microstructured reactor have been proposed. In a slurry reactor the average catalyst particle size can be between 20 and 200 µm.

All industrially operated catalysts, possibly with very rare exemptions, experience deactivation, i.e. a decline of the catalyst activity with time-on-stream (TOS). Often, the catalyst must be exchanged for a fresh one after some time of operation, typically between 0.5 and 5 years. For some reactions experiencing very rapid deactivation, a form of continuous or semi-continuous regeneration is needed. This is typical for FCC (fluid catalytic cracking) in the refinery where coke must be burned off after seconds of operation. However, continuous deactivation is also seen as a result of pick-up of impurities from the oil. In catalytic reforming to give gasoline the active Pt/Re or Pt/Sn system must be regularly regenerated by re-dispersing the active platinum on the support. For a cobalt Fischer-Tropsch catalyst, a study of a deactivated catalyst that has been operated in a slurry bubble column is reported in Applied Catalysis A: General, volume 354, pages 102-110, 2009. The main conclusion is that long-term deactivation is caused by carbon rich deposits.

Moderate experience regarding catalyst regeneration has been gained from operation of full-scale commercial (2000-20000 bpd production) or semi-commercial size Fischer-Tropsch reactors (200-2000 bpd) using cobalt type catalysts, particularly when using a slurry reactor type operation. The catalyst contains expensive cobalt and frequently also exotic promoters like platinum or rhenium. These are extremely expensive and due to the large size of modern GTL plants can also constitute a major portion of the world production. After unloading a deactivated catalyst it therefore becomes mandatory to reclaim as much as possible of the metals. These can be used in further catalyst production. Metals reclamation is usually a complicated process that involves multiple steps like chemical extraction or complexation. Further, the catalyst in itself will of course be destroyed. Therefore, a much more attractive solution would be to regenerate the catalyst for further use.

There are two main approaches to regeneration, in situ and ex situ, meaning inside the FT-reactor itself or separate from the reactor. In situ implies stopping the FT-reaction and using special conditions as to gas composition, and possibly temperature and pressure. Special regeneration configurations that we denote in situ in the present context are using part of the reactor volume in a continuous regeneration, or doing the same by taking a side stream from a slurry or fluidized-bed reactor that is exposed to regeneration conditions and continuously deployed into the reactor again. Although in situ regeneration has certain merits, it is seriously hampered by lack of flexibility in the conditions that can be applied. For instance, in a slurry FT-reactor one cannot use elevated temperature and/or oxygen in order not to destroy the liquid phase with possible severe consequences on the slurry operation. Further, design and operation of the reactor will be very complex to an extent that generally makes in situ regeneration impractical.

The use of hydrogen or a hydrogen-rich gas is an option that has been proposed, see e.g. EP0319625 where in situ regeneration of a cobalt FT-catalyst in low-temperature flowing hydrogen has been disclosed. However, the efficiency of such a regeneration is questionable, as deposited heavy hydrocarbons will not be removed to the extent needed.

In WO 2008/139407, a method for ex situ regeneration is described. The spent cobalt FT catalyst is first subjected to a dewaxing treatment, an oxidation treatment at a pressure of 4 to 30 bar(a) followed by a reduction treatment. The dewaxing is described as hydrogenolysis, solvent wash or extraction, or combinations thereof. Unfortunately, in WO 2008/139407, the effect of regeneration per se is not shown, only the relative results of using varying pressures during the oxidation stage.

SUMMARY OF THE INVENTION

The present invention is concerned with a simple and highly efficient way of ex situ regeneration of a deactivated FT catalyst. By ex situ regeneration, it is understood that the catalyst is removed from the reactor deployment, e.g. separated from the liquid in a slurry operation, and exposed to a dedicated regeneration procedure.

In certain aspects of the present invention, the ex situ regeneration is concerned with Co-based catalysts, in particular, supported Co-based catalysts.

According to the present invention, there is provided a process for the regeneration of deactivated catalyst from a Fischer-Tropsch synthesis reactor, the catalyst being a supported cobalt catalyst, the process comprising withdrawing a portion of deactivated catalyst together with liquid hydrocarbon from the reactor;

increasing the concentration of the catalyst in the liquid hydrocarbon at a temperature below 220° C. to produce a first deactivated catalyst composition containing from 45 to 99.5% of catalyst particles on a dry weight basis;

calcining the first deactivated catalyst composition, wherein the first deactivated catalyst composition is subjected to an oxidizing gas arranged to oxidize carbonaceous material contained in the deactivated catalyst, at a temperature in the range 150 to 600° C., into gaseous oxides of components of the carbonaceous material to produce a second deactivated catalyst composition; and reactivating the second deactivated catalyst composition to produce a regenerated catalyst.

In certain aspects of the present invention, the reactor is a slurry bubble column reactor in which $H_2$ and CO gases are supplied to a slurry in the reactor, the slurry comprising catalyst in suspension in a liquid hydrocarbon including the reaction products of the $H_2$ and CO, the catalyst being maintained in suspension in the slurry at least partly by the motion of the gas supplied to the slurry, and the withdrawal step comprises withdrawing a portion of the slurry from the reactor.

In certain aspects of the present invention, the amount of catalyst withdrawn in the withdrawal step represents, on a daily basis, between 0.01 and 10 wt % of the total catalyst inventory, preferably between 0.1 and 5 wt %.

In certain aspects of the present invention, the concentration step is conducted to produce a catalyst content of 70 to 99.5 wt %.

In certain aspects of the present invention, the concentration step is conducted to produce a wax content in the first deactivated catalyst composition in the range 1 to 55 wt %, preferably 2 to 45 wt %, more preferably 3 to 30 wt %.

In certain aspects of the present invention, the concentration step includes an operation selected from settling, filtration, magnetic separation, hydroclone separation and solvent extraction. In certain aspects, the operation is settling and is followed by removal of a portion of the liquid hydrocarbon. In certain aspects, the operation is solvent extraction and the solvent is a hydrocarbon, preferably a fraction of the liquid F-T product and/or paraffinic naphtha. In certain aspects, the solvent is added to a hydrocyclone.

In certain aspects of the present invention, the concentration step is carried out at a temperature below 200° C.

In certain aspects of the present invention, the hydrocarbon molecules in the first deactivated catalyst composition have an average number of carbon atoms significantly lower than the hydrocarbon molecules in the slurry reactor. In certain aspects, the number is less than 70% of the number of carbon atoms in the hydrocarbon molecules in the slurry reactor, preferably between 25 and 50%.

In certain aspects of the present invention, the oxidizing gas in the step of calcining the first deactivated catalyst composition is an oxygen-containing gas, preferably air. In certain aspects, the oxygen content of the oxygen-containing gas is from 2 to 30% by volume, preferably from 5 to 21%. In certain aspects, the step of calcining the first deactivated catalyst composition comprises conveying the first deactivated catalyst composition to a calciner, the calciner having a temperature of at least 150° C., preferably at least 250° C. In certain aspects, the calcination is carried out at a holding temperature between 150 and 600° C., preferably between 250 and 400° C. In certain aspects, the calcinations is conducted for a time in the range 0.01 to 10 hours, preferably 0.1 to 2 hours. In certain aspects, the calcincation is conducted in a rotary calciner, a stationary kiln or a fixed or fluidized bed. In certain aspects, the calcinations is conducted and arranged to reduce the content of carbonaceous material in the catalyst to <1 wt %. In certain aspects, the process comprises a second calcination step operated at a holding temperature higher than in the first calcination step.

In certain aspects of the present invention, the reactivation step comprises treatment with a reducing gas. In certain aspects, the reducing gas contains hydrogen. In certain aspects, the reactivation step is carried out at one or more holding temperatures in the range 200 to 600° C., preferably 250 to 500° C., more preferably 300 to 450° C.

In certain aspects of the present invention, the regenerated catalyst is re-introduced into the reactor following the reactivation step. In certain aspects, the regenerated catalyst is mixed with liquid hydrocarbons, preferably a fraction of the F-T product, before it is re-introduced into the reactor. In certain aspects, the regenerated catalyst is mixed with a liquid hydrocarbon withdrawn as a slurry from the reactor after the removal of most catalyst particles from the slurry, before it is re-introduced. In certain aspects, the proportion of the withdrawn catalyst that is regenerated and returned to the reactor is at least 60%, preferably at least 80%. In certain aspects, the regenerated catalyst particles will have a residence time distribution in which 80% of the catalyst inventory is deployed in the reactor for a period between 1 week and 10 years, preferably between 1 month and 5 years, more preferably between 2 months and 2 years.

In certain aspects of the present invention, the process further comprises reducing the fines content in the regenerated catalyst by using a filter, mesh or sifting in a gas flow, including using a fluidized-bed or air sifting equipment. In certain aspects, the content of fine catalyst particles in the re-introduced, regenerated catalyst is less than 3 wt % in the fraction below 20 μm, preferably less than 0.5 wt % in the fraction below 10 μm, most preferably less than 0.2 wt % in the fraction below 10 μm.

In certain aspects of the present invention, the catalyst comprises cobalt supported on a support consisting essentially of alumina or modified alumina. In certain aspects, the catalyst support material, prior to initial impregnation with cobalt, is γ-alumina. In certain aspects, the γ-alumina is impregnated with a source of a 2-valent metal and calcined to form a spinel. In certain aspects, the 2-valent metal is nickel or zinc in an amount of >5 wt %, preferably >10 wt %, of the final reduced catalyst. In certain aspects, the calcination is conducted at a temperature in the range 900° C. and 1250° C.

In certain aspects of the present invention, the regenerated catalyst after regeneration, contains an amount of cobalt, not more than 5 wt % different from the fresh catalyst after reduction, preferably less than 2 wt % different, more preferably less than 0.5 wt % different. In certain aspects, the catalyst incorporates a promoter, preferably rhenium or platinum.

In certain aspects of the present invention, the specific surface area of the prepared oxide catalyst after calcination but, before the reduction, comprising the cobalt oxide on the modified support, is up to 150 m$^2$/g or up to 80 m$^2$/g.

In certain aspects of the present invention, the pore volume of the fresh and regenerated catalysts in oxide forms is from 0.05 to 0.5 cm$^3$/g, preferably 0.1 to 0.4 cm$^3$/g.

In certain aspects of the present invention, the regenerated catalyst is protected by a coating of wax prior to being re-used.

In certain aspects of the present invention, a process for conducting a Fischer-Tropsch synthesis reaction to produce Fischer-Tropsch wax comprises introducing $H_2$ and CO to a Fischer-Tropsch reactor containing a supported cobalt catalyst, removing a wax product stream from the reactor, and regenerating the catalyst in a regeneration process of the present invention. In certain aspects, the regenerated catalyst is re-introduced into the reactor. In certain aspects, the reaction temperature is in the range 190-260° C. and the reaction pressure is in the range 10-70 bar. In certain aspects, the $H_2$/CO ratio of the gases supplied to the Fischer-Tropsch synthesis reactor is in the range 0.5 to 2.2. In certain aspects, the superficial gas velocity in the reactor is in the range 5 to 60 cm/s. In certain aspects, the product of the Fischer-Tropsch synthesis reaction is subsequently subjected to post-processing. In certain aspects, the post-processing is selected from de-waxing, hydro-isomerization, hydro-cracking, and combinations thereof.

In certain aspects, the present invention is directed to the use of a regenerated catalyst prepared by a process of the present invention in a Fischer-Tropsch synthesis process.

DETAILED DESCRIPTION OF THE INVENTION

According to the present invention, there is provided a process for the regeneration of deactivated catalyst from a Fischer-Tropsch synthesis reactor, the catalyst may be a supported cobalt catalyst, the process comprising withdrawing a portion of deactivated catalyst together with liquid hydrocarbon from the FT synthesis reactor, increasing the concentration of the catalyst in the liquid hydrocarbon at a temperature below 220° C. to produce a first deactivated catalyst composition containing from 45 to 99.5% of catalyst particles on a dry weight basis, calcining the first deactivated catalyst composition, wherein the first deactivated catalyst composition is subjected to an oxidizing gas arranged to oxidize carbonaceous material contained in the deactivated catalyst, at a temperature in the range 150 to 600° C., into gaseous oxides of components of the carbonaceous material to produce a second deactivated catalyst composition, and reactivating the second deactivated catalyst composition to produce a regenerated catalyst.

In this specification, the terms carbonaceous material or carbonaceous deposits on the catalyst refer to material containing carbon and hydrocarbon compounds that are lean in hydrogen and are not normally removed from the catalyst surface under operating conditions. Such carbonaceous materials include pure carbon, graphite, coke, polycarbon, condensed aromatics, olefins and long chained hydrocarbons, and may also include oxygen in their formulations.

It will be understood that while the liquid withdrawn in the withdrawal step will be essentially a hydrocarbon, up to a few percent may be oxygenates such as acids, alcohols, etc.

Preferably, the reactor is a slurry bubble column reactor in which $H_2$ and CO gases are supplied to a slurry in the reactor, the slurry comprising catalyst in suspension in a liquid hydrocarbon including the reaction products of the $H_2$ and CO, the catalyst being maintained in suspension in the slurry at least partly by the motion of the gas supplied to the slurry, and the withdrawal step comprises withdrawing a portion of the slurry from the reactor.

The withdrawal step may be carried out continually or intermittently. In operation, the reactor will inevitably contain catalyst particles in different states of activation. Typically, in practice, a reactor might contain a catalyst inventory of 300 to 1200 tons, and of this about 1 to 10 tons might be withdrawn for reactivation, per day.

Preferably, therefore, the amount of catalyst withdrawn for reactivation, on a daily basis, represents between 0.01 and 10 wt % of the total catalyst inventory, preferably between 0.1 and 5 wt %, more preferably between 0.2 and 2 wt %. Preferably, at least 60% of the withdrawn catalyst is regenerated and returned to the reactor, more preferably at least 80%, still more preferably at least 95%.

Typically, in the case of an F-T synthesis reaction conducted in a slurry bubble column reactor, the regenerated catalyst particles will have a residence time distribution in which 80% of the catalyst inventory is deployed in the reactor for a period between 1 week and 10 years, preferably between 1 month and 5 years, more preferably between 2 months and 2 years.

Preferably, the concentration step is conducted to produce a catalyst content of 70 to 99.5 wt %, preferably between 75 and 90 wt %, or alternatively between 95 and 99 wt %. Preferably, the concentration step is conducted to produce a wax content in the first deactivated catalyst composition in the range 1 to 55 wt % preferably 2 to 45 wt %, more preferably 3 to 30 wt %. There may be more than one concentration step. Preferably, the concentration step includes an operation selected from settling, filtration, magnetic separation, hydrocyclone separation and solvent extraction. The operation may comprise settling followed by removal of a portion of the liquid hydrocarbon, or may comprise solvent extraction where the solvent is a hydrocarbon, preferably a fraction of the liquid F-T product and/or paraffinic naphtha. The solvent may be added to a hydrocyclone. Preferably, the concentration step or each concentration step is carried out at a temperature below 200° C., more preferably below 180° C. Preferably, the hydrocarbon molecules in the first deactivated catalyst composition have an average number of carbon atoms significantly lower than the hydrocarbon molecules in the slurry reactor. Preferably, the number is less than 70% of the number of carbon atoms in the hydrocarbon molecules in the slurry reactor, preferably between 25 and 50%.

Conveniently, the oxidizing gas in the first calcination step is an oxygen-containing gas, preferably air. Preferably, the oxygen content of the oxygen-containing gas is from 2 to 30% by volume, more preferably from 5 to 21%. Preferably, the first calcination step comprises conveying the first deactivated catalyst composition to a calciner, the calciner having a temperature of at least 150° C., preferably at least 250° C. The first calcination step may be carried out at a holding temperature between 150 and 600° C., preferably between 250 and 400° C., more preferably between 270 and 350° C.

Preferably, the first calcination step is conducted for a time in the range 0.01 to 10 hours, preferably 0.1 to 2 hours. It may be carried out in a rotary calciner, a stationary kiln or a fixed or fluidised bed. Preferably, the first calcination step is conducted and arranged to reduce the content of carbonaceous material in the catalyst to <1 wt %.

There may be a further calcination step or steps, for example to remove coke deposits. The conditions may differ from the conditions in the first calcination step, e.g. at a higher holding temperature.

Surprisingly, the present inventors have found that highly efficient regeneration can be performed in a process without using dewaxing, and in which the oxidation (calcination) is carried out at atmospheric or moderate pressures. Further, a significant improvement in C5+ selectivity is experienced. Performing the calcination at atmospheric or close to atmospheric pressure significantly simplifies the process and conventional calcination means can be used. These include rotary calciners and stationary kiln calciners, but also other types such as pendulum, moving-bed, fluidized-bed and continuous fluidized-bed calciners. Calcination in this context means heat treatment at an elevated temperature. Normally this is carried out under oxidative conditions with air, but an inert gas or other gas compositions can also be used. To avoid large amounts of wax being evaporated, decomposed or oxidized during the calcination, the catalyst content of catalyst/wax mixture can be concentrated. This can be achieved by any convenient means, including settling, filtration, the use of a hydrocyclone and magnetic separation, preferably at least partly at a temperature where the wax is molten.

Preferably, the reactivation step comprises treatment with a reducing gas, preferably containing hydrogen, more preferably being composed of essentially hydrogen. Preferably, the reactivation step is carried out at one or more holding temperatures in the range 200 to 600° C., preferably 250 to 500° C., more preferably 300 to 450° C.

Preferably, following, the re-activation step, the regenerated catalyst is re-introduced into the reactor. Preferably, the regenerated catalyst is mixed with liquid hydrocarbons, preferably a fraction of the F-T product, before it is re-introduced into the reactor. Alternatively, the regenerated catalyst is mixed with a liquid hydrocarbon withdrawn as a slurry from the reactor after the removal of most catalyst particles from the slurry, before it is re-introduced.

As an alternative procedure, it is viable to wash the catalyst using an organic liquid, typically a hydrocarbon, before calcination. However, all the wax need not be removed and the calcination can take place at ambient or low pressure. It is most convenient to wash with a hydrocarbon fraction from the Fischer-Tropsch process itself, as this will already be available at the plant. A naphtha mainly with carbon numbers between C5 and C15 is convenient, but any liquid fraction that is able to remove the bulk of the wax will do. The washing itself can be done in any suitable tank or device, but it is particularly advantageous to apply a hydrocyclone. If naphtha is added to the hydrocyclone, a highly concentrated catalyst stream can be achieved for further treatment, typically calcination. Drying/evaporation can be performed before the calcination, to remove excess naphtha.

In a Fischer-Tropsch process it can be necessary to treat and purify the liquid primary hydrocarbon product for remains of catalyst before further processing. The catalyst can be in the form of very fine particles, e.g. in the size range <20 μm, or <5 μm or <1 μm, or soluble constituents. Such a "fines management" system can comprise techniques like settling, filtration, use of hydrocyclone, magnetic methods and chemical precipitation, or other suitable means. With any of these measures, separation of catalyst from the reactor liquid for regeneration can favorably be integrated with such fines management by ensuring that the primary product from the reactor contains a portion of the catalyst in the reactor. In this case, larger particles will be separated first and subjected to regeneration.

The process may therefore include the further step of reducing the fines content in the regenerated catalyst by using a filter, mesh or sifting in a gas flow, including using a fluidized-bed or air sifting equipment. Preferably, the content of fine catalyst particles in the re-introduced, regenerated catalyst is less than 3 wt % in the fraction below 20 μm, preferably less than 0.5 wt % in the fraction below 10 μm, most preferably less than 0.2 wt % in the fraction below 10 μm.

Suitable support materials for the catalyst include titania, silica, and alumina and various metal oxides and modified aluminas and mixtures thereof. These supports can be shaped in different ways to obtain a suitable form depending on the reactor type to be employed, e.g. by spray-drying techniques of an appropriate solution in order to obtain essentially spherical particles of appropriate size, e.g. 80% in the range between 30-200 μm. After spray-drying, the material is calcined at a high temperature to give the appropriate crystal size and pore structure.

The modified aluminas include alumina supports that have been modified by the addition of stabilization agents, treatment with silanes and other silicon compounds and various acid or base additions or wash procedures. One way of modifying the alumina is to add a divalent metal compound to the alumina or an alumina precursor followed by high temperature treatment. The high temperature treatment is preferably carried out at 700 to 1300° C., more preferably between 900 and 1250° C. Suitable divalent metal compounds include nickel, zinc and magnesium and other metals, which form a spinel with alumina Optionally, a promoter can be added, and rhenium is a well known promoter for cobalt Fischer-Tropsch catalysts. Other promoters besides rhenium, specifically, platinum, iridium or ruthenium, can be employed. It is also possible to add a second promoter such as lanthanum oxide or a mixture of oxides of the lanthanides or other compounds which are difficult to reduce.

In a preferred embodiment therefore, the catalyst comprises cobalt supported on a support consisting essentially of alumina or modified alumina. Preferably, the catalyst support material, prior to initial impregnation with cobalt, is γ-alumina, which may be impregnated with a source of a 2-valent metal and calcined to form a spinel. Preferably, the 2-valent metal is nickel or zinc in an amount of >10 wt % of the final reduced catalyst. Preferably, this calcination operation is conducted at a temperature in the range 900° C. and 1250° C.

Preferably, the regenerated catalyst after regeneration contains an amount of cobalt, not more than 5 wt % different from the fresh catalyst after reduction, preferably less than 2 wt % different, more preferably less than 0.5 wt % different. The catalyst may incorporate a promoter, preferably rhenium or platinum. Preferably, the specific surface area of the fresh oxide and regenerated catalyst, before the reactivation step comprising the cobalt on the modified support, is up to 150 $m^2/g$ or up to 80 $m^2/g$, and the pore volume of the fresh and regenerated catalysts in oxide form is from 0.05 to 0.5 $cm^3/g$, preferably 0.1 to 0.4 $cm^3/g$. The regenerated catalyst may be protected by a coating of wax prior to being re-used.

WO 2005/072866 discloses a method of producing an alumina-based supported catalyst, which comprises the following steps: a first impregnation step in which an initial alumina support material is impregnated with a source of a 2-valent metal capable of forming a spinel compound with alumina; a first calcination step in which the impregnated alumina support material is calcined at a temperature of at least 550° C. to produce a modified alumina support material; a second impregnation step in which the modified alumina support material is impregnated with a source of catalytically active metal; and a second calcination step in which the impregnated modified support material is calcined at a temperature of at least 150° C. This is then followed by a reduction step to activate the cobalt.

A study of this technique shows that in the present invention, the source of the 2-valent metal preferably comprises nickel or zinc in an amount of greater than 5 wt % of the final reduced catalyst, preferably greater than 10 wt %. Preferably, the initial catalyst support is alumina and more preferably substantially comprises γ-alumina. Preferably, the initial alumina support material has a specific surface area in the range 100 to 400 $m^2/g$, and a pore volume greater than 0.3 $cm^3/g$, preferably greater than 0.5 $cm^3/g$. Conveniently, after the first calcination step, the modified alumina support has a surface area of 20 to 80 $m^2/g$.

Before impregnation, the catalyst support may be pre-calcined at about 500° C. One convenient way of loading active metal and promoter onto the support in the present invention is by impregnation in one step, but multiple steps can also be employed, from a mixed aqueous solution of appropriate metal salts, generally of cobalt nitrate and perrhenic acid or alternatively ammonium perrhenate. The impregnation technique generally used is the pore filling or "incipient wetness" method, in which the solution is mixed with the dry support until the pores are filled. The definition of the end point of this method may vary somewhat from laboratory to laboratory so that an impregnated catalyst could have a completely dry appearance or a sticky snow-like appearance. However, in no instances are there any free flowing liquid present when the incipient wetness method is employed.

A number of alternative impregnation procedures are known in the art which use alternative solvents and chemicals, however, with the catalyst shown in the examples of this invention, the preferred procedure involves aqueous incipient wetness with solutions of cobalt nitrate ($Co(NO_3)_2 \cdot 6H_2O$) and perrhenic acid ($HReO_4$). Possible alternatives include using cobalt acetate(s), cobalt carbonate(s) cobalt halide(s), cobalt carbonyl(s), cobalt oxalate(s), cobalt phosphate(s), organic cobalt compounds, amine complexes, ammonium perrhenate, rhenium halide(s), rhenium carbonyl(s), industrial metal salt solutions, organic solvents and inorganic or organic binders etc. The solution may also encompass pH regulating agents, complexing agents, surfactants and other compounds that in some way influence the impregnation and following steps. Thus, ammonia or urea can be used.

Furthermore, the impregnation technique may encompass all available methods besides incipient wetness, such as precipitation, impregnation from slurry with surplus liquid, chemical vapour deposition etc. It is well known that the impregnation method may influence the dispersion of the active metal (cobalt) and hence the catalytic activity. Further, in the support preparation, as well as in subsequent steps, great care should be taken to limit the concentration of catalytic poisons for the Fischer-Tropsch reaction to acceptable levels. Such poisons typically encompass alkali metals, alkaline earth metals, sulfur and chloride.

According to one convenient procedure for making the catalyst, after impregnation of the alumina carrier material with a solution of a cobalt compound, it is dried at e.g. 80 to 120° C. to remove water from the catalyst pores and calcined at a relatively low temperature of 200 to 500° C., e.g. at 300° C., for 2 to 16 hours. The cobalt is then activated by a reduction step, typically by treating the catalyst with a reducing gas such as hydrogen at about 200 to 600° C., preferably 300 to 450° C., at pressures from atmospheric to 30 bar. However, the preferred reduction temperature will depend on the actual support used and the way in which the oxide catalyst is made.

Sometimes it can be convenient to split the reduction step(s) into further reduction steps or to include polishing by using a lower concentration of hydrogen, e.g. less than 5 vol %, in an inert carrying gas. A polishing step can reduce residual amounts of components from the impregnation, such as nitrate. CO can also be used as the reducing gas, either alone or mixed with $H_2$, and the reducing gas can be mixed with inerts, such as nitrogen, noble gases or steam and suitable temperatures and pressures should be applied.

If a fluidized bed reactor is used for activation, it may be convenient to use a recycle of at least a part of the reductive gas and a slight atmospheric total overpressure in order to achieve a suitable gas flow. It is also possible to use elevated total pressures, e.g. up to 8 bar or higher, or even the Fischer-Tropsch reactor pressure. Selection of the reduction temperature strongly depends on the presence and nature of promoters. It is well known that Re is highly efficient as a promoter in achieving high reducibilities at a conveniently reduced temperature.

Optimal activation procedures are described in a variety of patents and articles during the last 20 years. U.S. Pat. No. 4,670,414 describes increased activity of cobalt carbonyl-impregnated catalysts on alumina or silica by subjecting them to (A) reduction in hydrogen, (B) oxidation in an oxygen-containing gas, and (C) reduction in hydrogen, claiming this significantly improved the catalysts performance in Fischer-Tropsch. U.S. Pat. No. 4,729,981 describes the use of the same method on a cobalt or nickel containing catalyst on refractory metal oxide support. US 2004/0127585 describes co-feeding parts-per-million quantities of carbon monoxide along with the reducing gas to reduce the loss of liquid from the slurry and the production of methane. U.S. Pat. No. 7,045,554 describes how low levels of oxygen deactivate the smaller more unstable metal crystallites present in the catalyst matrix, thus giving a more stable catalyst.

Preferably, the specific surface area of the prepared oxide catalyst of the invention, i.e. the catalyst after calcination but before reduction, comprising cobalt oxide, is (using a modified support) up to 150 $m^2/g$ or up to 80 $m^2/g$, and the pore volume of this prepared catalyst is from 0.05 to 0.5 $cm^3/g$, preferably 0.1 to 0.4 $cm^3/g$. Preferably, the pore diameter of the prepared catalyst is at least 10 nm, preferably 18 nm.

The present invention extends to a process for conducting a Fischer-Tropsch synthesis reaction to produce Fischer-Tropsch wax which comprises $H_2$ and CO to a Fischer-Tropsch reactor containing a supported cobalt catalyst, removing a wax product stream from the reactor, and regenerating the catalyst in a regeneration process according to the present invention previously discussed.

Preferably, the regenerated catalyst is re-introduced into the reactor.

Preferably, therefore, the reaction is a three-phase reaction in which the reactants are gaseous, the product is at least partially liquid and the catalyst is solid, and is carried out in a slurry bubble column reactor. Preferably, the $H_2$ and CO are supplied to a slurry in the reactor, the slurry comprising the catalyst in suspension in a liquid including the reaction products of the $H_2$ and CO, the catalyst being maintained in suspension in the slurry at least partly by the motion of the gas supplied to the slurry.

The reaction temperature may be in the range 190 to 260° C., preferably 210 to 240° C., and the pressure may be in the range 10 to 70 bar, preferably 20 to 40 bar. The $H_2/CO$ ratio of the gas fed to the reactor may be in the range 0.5 to 2.2, preferably 1.2 to 1.95, and the superficial gas velocity may be in the range 5 to 60 cm/s, preferably 20 to 40 cm/s. The products can be subjected to various post-processing operations, such as filtration, de-waxing, hydroisomerization and/or hydro-cracking.

In general, catalyst particles operating in an FT-reactor, in particular a fluidized-bed or slurry bubble column, will be subject to attrition with time. Attrition can be described as a physical wear of the particles caused by shear forces in the reactor, collision with other particles or reactor internals, etc. Fine particles can be created by abrasion of the surface, but larger fractions and splitting or crushing of particles can also occur. Chemical attrition can also be an important factor e.g. by weakening of the catalyst particles with time. In an FT-operation, the steam created, acidic components such as $CO_2$ and small amounts of formed organic acids can cause such chemical attack. Normally, therefore, attrition results in a certain proportion of fine catalyst particles as part of any deactivated catalyst. These fine particles are normally not beneficial for re-loading into the reactor after regeneration. In a slurry operation, the content of fine catalyst particles to be reloaded is preferably reduced to less than 3 wt % in the fraction below 20 nm, preferably less than 0.5 wt % in the fraction below 10 nm, most preferably less than 0.2 wt % in the fraction below 10 μm.

EXAMPLES

The present invention may be carried into practice in various ways and will now be illustrated in the following non-limiting Examples.

In the Examples, all the catalyst testing was performed in a fixed bed laboratory unit with four parallel fixed-bed reactors. Approximately 1 g of catalyst particles, fresh or regenerated after the calcination step, in a size fraction between 53 and 90 microns were mixed with 20 g of inert SiC. Reduction was performed in situ at 350° C. and 1 bar(a) for 16 h in hydrogen. The subsequent Fischer-Tropsch performance step was carried out in a mixture of hydrogen and CO at a ratio of 2:1. After 20 h on stream at 210° C. and 20 bar total pressure, the space velocity was adjusted to give an estimated conversion level of CO between 45 and 50% after 100 h. It is very important to perform selectivity, as well as activity, comparisons at the same level of conversion, as the level of steam generated in the reaction has a profound influence on the catalyst performance. In examples C a modified procedure is used in which used and drained catalyst is loaded directly to the test reactor and some catalysts were exposed to in situ calcination.

All examples are concerned with FT catalysts containing at least some reduced and active cobalt metal and contained in wax, except for the C2-O oxide catalyst precursor. For a freshly made and reduced catalyst, the wax is deliberately added to avoid reoxidation of the cobalt during transport and storage. For a used and deactivated catalyst, the wax is the heavy product part of the FT reaction itself contained in the slurry reactor, and therefore a natural constituent of the unloaded catalyst. The wax may fill the pores of the catalyst particles, the space between them or fully cover a given assembly (lump) of catalyst particles. The deactivated catalysts are from a long-term run in a semi-commercial slurry type FT-plant.

Example A

Removal of Wax and Calcinations

The amount of wax contained in and between used catalyst particles was reduced by loading a sample to a Soxlet extraction funnel and heating the sample to 85° C. in air to let wax drain off. Thereafter the sample was transferred to a ceramic crucible and calcined in air in a kiln at 300° C. for 16 h. Some results are shown in Table 1, including the same procedure applied to freshly reduced catalyst samples contained in FT-wax for comparison. The samples are denoted as follows:

C1-R: an oxide catalyst on γ-alumina support subjected to activation by reduction in hydrogen;
C2-O: an oxide catalyst on a spinel type support;
C2-R: an oxide catalyst on a spinel type support subjected to activation by reduction in hydrogen; and
C2-U1 to C2-U4: consecutively used catalysts, on a spinel type support, in wax from an extended Fischer-Tropsch test in a slurry bubble column reactor.

TABLE 1

| | Fresh catalyst C1-R | Fresh catalyst C2-R | Fresh catalyst C2-R**** | C2 used Sample C2-U1 | C2 used Sample C2-U2 | C2 used Sample C2-U2** | C2 used Sample C2-U3 | C2 used Sample C2-U3*** | C2 used sample C2-U4**** |
|---|---|---|---|---|---|---|---|---|---|
| Draining | | | | | | | | | |
| Catalyst amount (g)* | 129.45 | 12.36 | 23.88 | na | | | 7.61 | 11.04 | 19.96 |
| After draining (g) | 89.07 | 5.74 | 9.04**** | na | | | 5.99 | 7.06*** | 15.33**** |
| Difference (g) | 40.38 | 6.62 | 14.84 | na | | | 1.62 | 3.98 | 4.63 |
| Difference (%) | 31.2 | 53.6 | 62.1 | na | | | 21.3 | 36.1 | 23.2 |
| Calcination | | | | | | | | | |
| Before calcining (g) | 89.07 | 5.74 | 9.04 | 5.96 | 146.59 | 8.13 | 3.65 | 7.06 | 15.33 |
| After calcining (g) | 51.2 | 4.35 | 8.90 | 4.85 | 111.95 | 6.35 | 3.12 | 6.82 | 14.67 |
| Difference (g) | 37.87 | 1.39 | 0.14 | 1.11 | 34.64 | 1.78 | 0.53 | 0.24 | 0.66 |
| Difference (%) | 42.5 | 24.2 | 1.5 | 18.6 | 23.6 | 21.98 | 14.5 | 3.4 | 4.3 |
| Catalyst concentration before draining (wt %) | 39.6 | 35.2 | 37.3 | na | na | na | 64.5 | 61.8 | 73.5 73.5 |

TABLE 1-continued

Wax draining and calcination

|  | Fresh catalyst C1-R | Fresh catalyst C2-R | Fresh catalyst C2-R**** | C2 used Sample C2-U1 | C2 used Sample C2-U2 | C2 used Sample C2-U2** | C2 used Sample C2-U3 | C2 used Sample C2-U3*** | C2 used sample C2-U4**** |
|---|---|---|---|---|---|---|---|---|---|
| Catalyst concentration after draining (wt %)***** | 57.5 | 75.8 | 98.5**** | 81.4 | 76.4 | 74.2 | 81.9 | 96.6*** | 95.7 |

*Total weight mixed with wax.
**Calcined at 500° C. in stead of 300° C.
***Using extraction by 50/50 wt % cyclohexane/n-heptane to remove wax instead of draining.
****Using extraction by 100% n-heptane to remove wax instead of draining.
*****Approximate. Assuming that all carbonaceous material has been removed by calcination.
na: Data not available.

The weight reduction by draining a fresh sample was 53.6% (C2-R) compared to 21.3 for a used samples (C2-U3). This reflects mainly the concentration of catalyst particles in the wax as the used sample was taken at the bottom of a reactor sample settled in a container. Further calcination of fresh catalyst C2-R gave 24.2% reduction in weight, whereas the used catalysts gave about 15% reduction (C2-U3). A small part of the weight loss upon calcination can be due to coke accumulated during operation instead of wax. For the C2-U2 sample, calcination was performed directly without any initial draining Calcination at 500° C. gives a weight reduction comparable to 300° C. It should be noted that much more wax can be removed from the sample by using a solvent as the residual weight loss upon calcination is only 3.4 and 4.3 wt % (C2-U3 * and C2-U4 **) for used samples and 1.5 wt % (C2-R) for a fresh sample. The figures for used catalysts also reflect an upper value for the coke content.

Example B

Activity Tests

The catalytic activity was tested in a bench-scale fixed-bed reactor as described separately. Data were compared after 100 h time on stream at about 45% conversion.

TABLE 2

Activity testing*

| Catalyst | Wax draining | Calcination | Relative activity | Relative C5+ selectivity |
|---|---|---|---|---|
| C2-O | — | — | 0.96 | 0.918 |
| C2-R | yes | no | 0.87; 0.91 | 0.924; 0.925 |
| C2-R | yes | yes | 0.90 | 0.942 |
| C2-U1 | yes | no | 0.66 | 0.950 |
| C2-U1 | yes | yes | 0.88; 0.89 | 0.965; 0.963 |
| C2-U2 | no | yes | 0.82 | 0.975 |
| C2-U2-250** | no | yes | 0.74 | 0.960 |
| C2-U2-400** | no | yes | 0.68 | 0.959 |
| C2-U2-500** | no | yes | 0.65 | 0.963 |
| C2-U2*** | solvent | no | 0.44 | 0.920 |
| C2-U2*** | solvent | yes | 0.94 | 0.977 |
| C2-U3 | yes | no | 0.48 | 0.899 |
| C2-U3 | yes | yes | 0.83; 0.86 | 0.970; 0.974 |
| C2-U3*** | solvent | yes | 1.06 | 0.962 |

TABLE 2-continued

Activity testing*

| Catalyst | Wax draining | Calcination | Relative activity | Relative C5+ selectivity |
|---|---|---|---|---|
| C2-U4 | yes | yes | 0.87 | 1.26 |
| C2-U4*** | solvent | yes | 1.00 | 0.963 |

*Two values in a given entry shows reproducibility of the fixed-bed test of the same drained and calcined sample.
**Calcined at 250, 400 or 500° C.
***Using extraction by 50/50 wt % cyclohexane/n-heptane to remove wax instead of draining.

Looking at the C2-U1, and C2-U3 samples, there is a significant increase in the relative catalyst activity after calcination of the deactivated catalyst: 0.66 up to 0.88/0.89 and 0.48 up to 0.83/0.86, respectively. Most of the initial relative activity of 0.90 of the freshly reduced catalyst as loaded into the reactor has been regained. As it is expected that carbon rich deposits is the main cause of deactivation, the present simple procedure is efficient in removing at least a critical portion of this deposit. Calcination at 400 or 500° C. seems to be too high as it expectedly leads to sintering of active cobalt metal particles. 250° C. gives a positive effect on the activity, but 300° C. is more effective. As there are no carbon deposits on the fresh catalyst, there is no effect upon calcination.

It might also be observed that the catalysts C2-U1 and C2-U3 which have not experienced calcination have low activities. This is in spite of the hydrogen treatment that was conducted at 350° C. for as long as 16 h. Therefore it would seem that hydrogen treatment is not efficient in regenerating the catalyst, and do these results serve as comparative examples. In fact, the activities of about 0.63 and 0.48 are only moderately higher than the original activities for the same samples as observed in the long-term slurry run where the deactivation took place.

The use of a solvent to remove wax before calcination has a very positive effect on both activity and selectivity. In fact, the relative activity has increased to a level (1.06 for C2-U2 and 1.00 for C2-U4) higher than the freshly loaded catalyst (C2-R).

A remarkable effect is that the selectivity towards C5+ products has improved to the range 0.959-0.975 in relative selectivity upon calcination of deactivated catalysts, an increase of about 4% from the fresh catalyst. Such an increase in selectivity will have a significant effect on the product yield of a GTL plant. Applying draining and calcination to the fresh catalyst (C2-R) does not appear to improve activity over just draining, and the effect on selectivity is moderate. It appears that the positive effect of the procedure described here is characteristic for a used and deactivated catalyst.

Example C

In Situ Calcination and Activity Tests

The in situ calcination is performed in the fixed-bed reactor at 300° C. and 1 bar(a) for 16 h using a ramp rate of 2° C./min and an air flow rate of 250 ml/min, followed by standard reduction and FT testing.

TABLE 3

Activity testing using in situ calcination in the fixed-bed reactor.

| Catalyst | Wax draining | Calcination | Relative activity | Relative C5+ selectivity |
|---|---|---|---|---|
| C2-U1 | yes | no | 0.66 | 0.950 0.950 |
| C2-U1 | yes | ex-situ | 0.88/0.89 | 0.950/0.963 |
| C2-U1 | yes | in-situ | 0.98 | 0.925 |
| C2-U2 | yes | no | 0.46 | 0.917 |
| C2-U2 | yes | ex-situ | 0.82 | 0.975 |
| C2-U2 | yes | in-situ* | 0.75 | 0.951 |
| C2-U3 | yes | no | 0.48 | 0.899 |
| C2-U3 | yes | ex-situ | 0.83/0.86 | 0.970/0.974 |
| C2-U3 | yes | in-situ | 0.92 | 0.939 |

*Using very low gas flow during calcination.

In carrying out the regenerative calcination in the fixed-bed test reactor a clear positive effect on the relative activity can be seen, even more pronounced than carrying out the calcination in a dedicated calcination kiln. The details of the calcination conditions are therefore probably important. One distinction between the two calcination procedures is that in the fixed-bed, a forced flow of air passes through the sample at all times, including during heat-up. Using a low flow is not as efficient as using a high flow during in situ calcination. The very high selectivities found in Example B cannot be seen for the in situ calcined catalysts. This observation is probably due to a less efficient mixing with the inert (SiC), as the catalyst particles before loading stick together due to wax residuals. A detailed analysis of the data shows clear signs of diffusion limitations in these experiments.

Example D

Porosity

The pore volume and surface area of catalyst after regeneration compared to fresh catalyst is shown in Table 4.

TABLE 4

Pore characteristics before and after regeneration

| Catalyst/support | Pore Volume (cm³/g) | Surface Area (m²/g) |
|---|---|---|
| C2-support | 0.27 | 55.4 |
| C2-O | 0.16 | 43.3 |
| C2-U1-calcined | 0.17 | 43.1 |
| C2-U2-calcined | 0.16 | 42.8 |

It can be observed that no detectable changes to pore volume or surface area are seen for the fresh oxide catalyst compared to regenerated catalyst after the calcination step.

The invention claimed is:

1. A process for the regeneration of deactivated catalyst from a Fischer-Tropsch synthesis reactor, the catalyst being cobalt supported on a modified alumina support comprising a spinel phase, the process comprising the steps of:
    withdrawing a portion of deactivated catalyst together with liquid hydrocarbon from the Fischer-Tropsch synthesis reactor;
    increasing the concentration of the deactivated catalyst in the liquid hydrocarbon at a temperature below 220° C. to produce a first deactivated catalyst composition containing from 45 to 99.5% of catalyst particles on a dry weight basis;
    calcining the first deactivated catalyst composition at a temperature in the range 150 to 600° C., wherein the first deactivated catalyst composition is subjected to an oxidizing gas arranged to oxidize carbonaceous material contained in the deactivated catalyst into gaseous oxides of components of the carbonaceous material to produce a second deactivated catalyst composition; and
    reactivating the second deactivated catalyst composition to produce a regenerated catalyst.

2. The process of claim 1, wherein the reactor is a slurry bubble column reactor in which $H_2$ and CO gases are supplied to a slurry in the reactor, the slurry comprising catalyst in suspension in a liquid hydrocarbon including the reaction products of the $H_2$ and CO, the catalyst being maintained in suspension in the slurry at least partly by the motion of the gas supplied to the slurry, and the withdrawal step comprises withdrawing a portion of the slurry from the reactor.

3. The process of claim 1, wherein the amount of catalyst withdrawn in the withdrawal step represents, on a daily basis, between 0.01 and 10 wt % of the total catalyst inventory.

4. The process of claim 1, wherein the concentration step is conducted to produce a catalyst content of 70 to 99.5 wt %.

5. The process of claim 1, wherein the concentration step is conducted to produce a wax content in the first deactivated catalyst composition in the range 1 to 55 wt %.

6. The process of claim 1, wherein the concentration step includes an operation selected from settling, filtration, magnetic separation, hydroclone separation, and solvent extraction.

7. The process of claim 6, wherein the operation is settling and is followed by removal of a portion of the liquid hydrocarbon.

8. The process of claim 6, wherein the operation is solvent extraction and the solvent is a hydrocarbon.

9. The process of claim 8, wherein the solvent is added to a hydrocyclone.

10. The process of claim 1, wherein the concentration step is carried out at a temperature below 200° C.

11. The process of claim 2, wherein the hydrocarbon molecules in the first deactivated catalyst composition have an average number of carbon atoms significantly lower than the hydrocarbon molecules in the slurry reactor.

12. The process of claim 11, wherein the average number is less than 70% of the number of carbon atoms in the hydrocarbon molecules in the slurry reactor.

13. The process of claim 1, wherein the oxidizing gas in the first calcination step is an oxygen-containing gas.

14. The process of claim 13, wherein the oxygen content of the oxygen-containing gas is from 2 to 30% by volume.

15. The process of claim 1, wherein the first calcination step comprises conveying the first deactivated catalyst composition to a calciner, the calciner having a temperature of at least 150° C.

16. The process of claim 1, wherein the first calcination step is carried out at a holding temperature between 150 and 600° C.

17. The process of claim 1, wherein the first calcination step is conducted for a time in the range of 0.01 to 10 hours.

18. The process of claim 1, wherein the first calcination step is conducted in a rotary calciner, a stationary kiln, a fixed bed, or a fluidized bed.

19. The process of claim 1, wherein the first calcination step is conducted and arranged to reduce the content of carbonaceous material in the catalyst to less than 1 wt %.

20. The process of claim 1, further comprising a second calcination step operated at a holding temperature higher than the temperature in the first calcination step.

21. The process of claim 1, wherein the reactivation step comprises treatment with a reducing gas.

22. The process of claim 21, wherein the reducing gas contains hydrogen.

23. The process of claim 1, wherein the reactivation step is carried out at one or more holding temperatures in the range of 200 to 600° C.

24. The process of claim 1, further comprising re-introducing the regenerated catalyst into the reactor after the reactivation step.

25. The process of claim 24, further comprising mixing the regenerated catalyst with liquid hydrocarbonsbefore it is re-introduced into the reactor.

26. The process of claim 24, further comprising mixing the regenerated catalyst with a liquid hydrocarbon withdrawn as a slurry from the reactor after the removal of most catalyst particles from the slurry, before it is re-introduced.

27. The process of claim 24 wherein a proportion of the withdrawn catalyst that is regenerated and returned to the reactor is at least 60%.

28. The process of claim 24, wherein the regenerated catalyst particles have a residence time distribution in which 80% of the catalyst inventory is deployed in the reactor for a period between 1 week and 10 years.

29. The process of claim 24 further comprising the step of reducing a fines content in the regenerated catalyst by using a filter, mesh, or sifting in a gas flow.

30. The process of claim 29, wherein the content of the fine catalyst particles in the re-introduced, regenerated catalyst is less than 3 wt % in a fraction below 20 μm.

31. The process of claim 1, wherein the catalyst support material, prior to initial impregnation with cobalt, is γ-alumina.

32. The process of claim 31, wherein the γ-alumina is impregnated with a source of a 2-valent metal and calcined to form a spinel.

33. The process of claim 32, wherein the 2-valent metal is nickel or zinc in an amount of greater than 5 wt %.

34. The process of claim 32 wherein the calcination is conducted at a temperature in the range of 900° C. and 1250° C.

35. The process of claim 1, wherein the regenerated catalyst contains an amount of cobalt of not more than 5 wt % different from a fresh catalyst of the deactivated catalyst after reduction.

36. The process of claim 1, wherein the catalyst incorporates a promoter.

37. The process of claim 1, wherein the specific surface area of the prepared oxide catalyst after calcination but, before the reduction, comprising the cobalt oxide on the modified support, is up to 150 $m^2/g$ or up to 80 $m^2/g$.

38. The process of claim 1, wherein the pore volume of the regenerated catalysts in oxide forms is from 0.05 to 0.5$cm^3/g$.

39. The process of claim 24, further comprising coating the regenerated catalyst in a protective coating of wax prior to being re-introduced.

40. A process for conducting a Fischer-Tropsch synthesis reaction to produce Fischer-Tropsch wax which comprises $H_2$ and CO to a Fischer-Tropsch reactor containing a supported cobalt catalyst, removing a wax product stream from the reactor, and regenerating the catalyst in a regeneration process as claimed in claim 1.

41. The process of claim 40, wherein the regenerated catalyst is re-introduced into the reactor.

42. The process of claim 40 wherein the reaction temperature is in the range of 190-260° C. and the reaction pressure is in the range of 10-70 bar.

43. The process of claim 40, wherein a $H_2/CO$ ratio of the gases supplied to the Fischer-Tropsch synthesis reactor is in the range of 0.5 to 2.2.

44. The process of claim 40, wherein a superficial gas velocity in the reactor is in the range of 5 to 60 cm/s.

45. The process of claim 40, wherein a product of the Fischer-Tropsch synthesis reaction is subsequently subjected to post-processing.

46. The process of claim 45, wherein the post-processing is selected from de-waxing, hydro-isomerization, hydro-cracking, and combinations thereof.

47. A method for the production of hydrocarbons, the method comprising:
withdrawing a portion of deactivated catalyst together with liquid hydrocarbon from the Fischer-Tropsch synthesis reactor, the portion of deactivated catalyst comprising cobalt supported on a modified alumina support comprising a spinel phase;
increasing the concentration of the deactivated catalyst in the liquid hydrocarbon at a temperature below 220° C. to produce a first deactivated catalyst composition containing from 45to 99.5% of catalyst particles on a dry weight basis;
calcining the first deactivated catalyst composition at a temperature in the range 150 to 600° C., wherein the first deactivated catalyst composition is subjected to an oxidizing gas arranged to oxidize carbonaceous material contained in the deactivated catalyst into gaseous oxides of components of the carbonaceous material to produce a second deactivated catalyst composition;
reactivating the second deactivated catalyst composition to produce a regenerated catalyst; and
subjecting $H_2$ and CO gases to a Fischer-Tropsch synthesis process in a reactor in the presence of the regenerated catalyst.

* * * * *